US00PP10495P

Jnited States Patent [19]

)anziger

[11] Patent Number: Plant 10,495

[45] Date of Patent: Jul. 14, 1998

4] NEW GUINEA IMPATIENS PLANT NAMED 'DANIMIN'

5] Inventor: Gaby Danziger, Nir Zvi, Israel

3] Assignee: Danziger "Dan" Flower Farm, Post Beit Dagan, Israel

1] Appl. No.: 677,851

2] Filed: Jul. 10, 1996

1] Int. Cl.[6] ..... A01H 5/00

2] U.S. Cl. ..... Plt./87.6

8] Field of Search ..... Plt./87.6

[56] References Cited

U.S. PATENT DOCUMENTS

P.P. 8,368 9/1993 Bull ..... Plt./87.6

*Primary Examiner*—Howard J. Locker
*Assistant Examiner*—Kent L. Bell
*Attorney, Agent, or Firm*—Foley & Lardner

[57] ABSTRACT

A new and distinct cultivar of Impatiens plant named Danimin, characterized by the combined features of very large, pink flowers with red-purple centers, solid dark green leaves, wide growth habit with excellent self branching, early flowering, and its suitability for pot or hanging basket culture.

1 Drawing Sheet

1

The present invention relates to a new and distinctive ltivar of Impatiens plant, botanically known as Impatiens, mmercially known as New Guinea Impatiens, and known the cultivar name 'Danimin'.

Danimin was developed by the inventor Gaby Danziger in controlled breeding program in Mishmar Hashiba, Israel crossing the cultivar identified as '1-98' (seed parent), th the cultivar identified as '3-16' (pollen parent). Both ltivars are proprietary.

Asexual reproduction of the new cultivar by leaf cuttings ten by the inventor at Mishmar Hashiva, Israel has shown it the unique features of this new impatiens plant are bilized and are reproduced true to type in successive ppagations.

The following characteristics in combination distinguish new impatiens plant from both its parent varieties and ier cultivated impatiens of this type known and used in the riculture industry:

1. Very large, light pink flowers, with red-purple centers.
2. Solid dark green leaves.
3. Wide or spreading growth habit, with excellent self inching.
4. Early and prolific flowering.
5. Its suitability for pot or hanging basket culture.

In the accompanying colored photographic drawings, the otograph at the top of the sheet comprises a top view owing the overall appearance of a typical plant the new tivar, with the photograph at the bottom of the sheet owing flowers and foliage in much greater detail. In the otos, true flower color is most accurately depicted in the view of the plant.

Danimin is particularly distinguished by its very large it pink flowers, early and prolific flowering, and its solid k green leaves, and those combined characteristics are que. When compared to the cultivar 'Melanie', disclosed U.S. Plant Pat. No. 8,368, 'Danimin' has a darker red-ple center eye, a larger flower, a narrower leaf, and a re compact growth habit.

The following is a detailed description of my new impa-is cultivar based on plants produced under commercial ctice in Mishmar Hashiva, Israel. The plants were grown a net-covered greenhouse during spring time, with a timum temperature of 30° C. and a minimum tempera-of 18° C.

Color references are made to The Royal Horticulture iety Color chart except where general terms of ordinary ionary significance are used.

2

Parentage: Seedling from '1-98'×'3-16'.

Propagation:

*Type cutting.*—Leaf cuttings.

*Time to initiate roots.*—7–8 days at 25° C. in summer and 8–9 days at 20° C. in winter.

*Rooting habit.*—Roots well, about 20–25 roots per plant, each approximately, 2–3 cm in length and 0.5–1.0 mm thick.

Plant description:

*Form*—Plant is relatively large in diameter with good self branching. As measured 4 months after planting a single young plant in a 16 cm pot, the plant was approximately 26–50 cm in height and 21–60 cm in width.

*Habit.*—Wide or spreading growth habit.

*Foliage (mature).*—Size: Approximately 80 mm long and 30 mm wide. Shape: Oblong, leaf apex is acuminate; texture is typical for the species. Margin: Serrated. Color: Young foliage, top side 139A, under side 137C; mature foliage, top side 139A, under side 137C. Venation: Primary vein is 59C; top midrib is 66C.

Flowering description:

*Flowering habits.*—Prolific flowering, with many flowers developing above the foliage, and covering the entire plant. Initiation of flower buds takes about 51 days after planting.

*Natural flowering season.*—Flowering is year around in temperatures between 5C. and 25C.; not tolerant to frost.

*Flower buds.*—There are 3–6 buds on each axil, with each bud before opening being oval shape and 2.0–2.5 cm in length along its major axis. Buds are carried on red pedicels 37 mm in length; red-purple spurs (RHS 59A) are oval shaped and 3.5–5.0 cm in length.

*Flowers borne.*—The flowers are carried on stems that terminate above the foliage.

*Quality of flowers.*—Very heavy flowering

*Petals.*—Shape: Typical, two heart-shaped pairs of petals, with each petal being approximately 2.5–3.5 cm in width and 2.5–3.0 cm in length; and the remaining petal 3.5–4.0 in width and 2.0–2.5 cm in length. Color: Top side when opening 65B, fading to 65C; under side 65B; center eye is 58A. Number of petals: 5. Size of flowers: Very large, approximately 6.5 cm in diameter.

*Reproductive organs.*—Stamens: One (1) in number. Anther shape: Round, color red. Pollen color: White. Pistils: Stigma shape: Round, color nearly white. Style color: Green. Ovaries: Four, 1 mm in size, green in color.

*Disease resistance.*—No abnormal disease problems have been noted to date.

I claim:

1. A new and distinct cultivar of impatiens plant named 'Danimin', as illustrated and described.

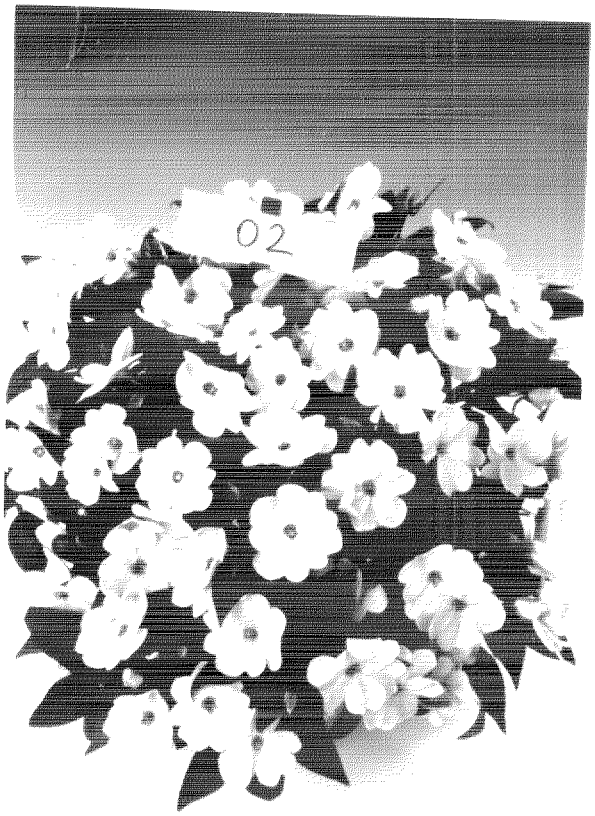
02
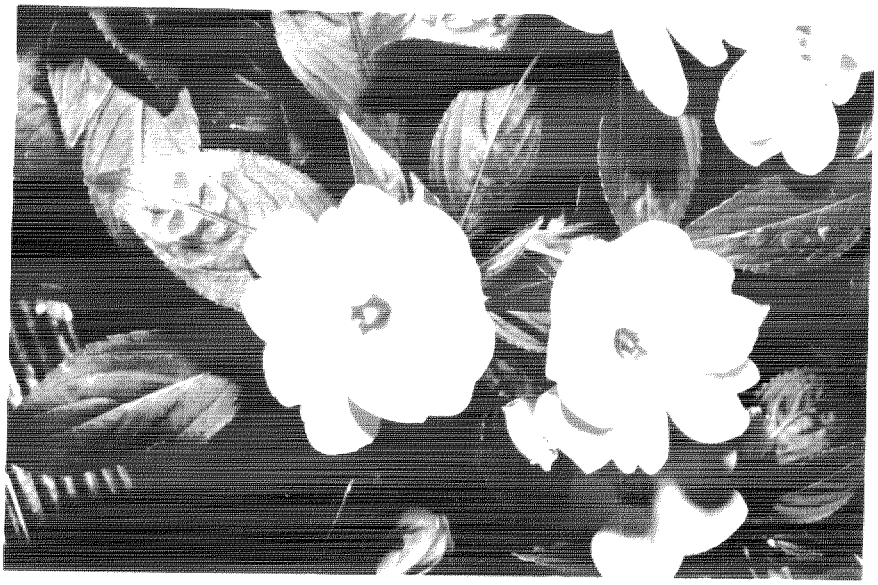

* * * * *